US008727605B2

(12) United States Patent
Bucher

(10) Patent No.: US 8,727,605 B2
(45) Date of Patent: May 20, 2014

(54) ONE-WAY MIXER HOMOGENIZER, EXTRACTOR, FRACTIONER OR SLURRY PRODUCER

(75) Inventor: Franz Gregor Bucher, Zug (CH)

(73) Assignee: Medic Tools AG, Zug (CH)

( * ) Notice: Subject to any disclaimer, the term of this patent is extended or adjusted under 35 U.S.C. 154(b) by 1290 days.

(21) Appl. No.: 11/577,832

(22) PCT Filed: Nov. 18, 2005

(86) PCT No.: PCT/CH2005/000685
§ 371 (c)(1),
(2), (4) Date: Apr. 24, 2007

(87) PCT Pub. No.: WO2006/076820
PCT Pub. Date: Jul. 27, 2006

(65) Prior Publication Data
US 2008/0253223 A1   Oct. 16, 2008

(30) Foreign Application Priority Data

Jan. 21, 2005 (CH) ............................................ 92/05
Nov. 7, 2005 (CH) ...................................... 1782/05

(51) Int. Cl.
*B01F 7/00* (2006.01)
*B01F 9/00* (2006.01)
*B02C 18/00* (2006.01)

(52) U.S. Cl.
USPC ........... 366/230; 366/302; 366/305; 422/258; 241/199.1

(58) Field of Classification Search
USPC .......... 366/130, 304, 305, 230, 302; 422/258, 422/259, 500; 241/82.1, 82.3, 89.3, 199.12, 241/DIG. 27, DIG. 30, 169.1, 199.1
See application file for complete search history.

(56) References Cited

U.S. PATENT DOCUMENTS

| 533,141 | A | * | 1/1895 | Prest | 241/169.1 |
| 605,922 | A | * | 6/1898 | Schule | 99/620 |
| 1,444,346 | A | * | 2/1923 | Kohr | 241/82.1 |
| 1,732,618 | A | * | 10/1929 | Royle | 241/82.1 |
| 1,821,344 | A | * | 9/1931 | Kautzman et al. | 198/814 |
| 2,285,721 | A | * | 6/1942 | Karp | 241/88 |
| 3,349,966 | A | * | 10/1967 | Schwartzman | 222/80 |
| 3,581,790 | A | * | 6/1971 | Conte | 241/88.1 |

(Continued)

FOREIGN PATENT DOCUMENTS

| EP | 0590219 | 10/1992 |
| EP | 1361917 | 10/2001 |
| WO | 2004035191 | 4/2004 |

OTHER PUBLICATIONS

English translation of WO 2004/035191 by Bucher (PCT/CH2003/000675), submitted to PTO Mar. 3, 2005 with U.S. Appl. No. 10/526,647.*

*Primary Examiner* — Charles E Cooley
(74) *Attorney, Agent, or Firm* — Volpe and Koenig, P.C.

(57) ABSTRACT

A single-use mixer or homogenizer is provided that includes a container provided with a lid which is provided as a compression element (29) for substances (45) in the container (1). The compression element (29) is rotatably arranged in relation to the container (1). The substances (45) are pressed and ground through the sieve (13) into the collecting chamber (27) by the rotation of the compression element (29), and can be removed by a pipette (43) which passes through both the compression element (29) and the cover on the sieve (13).

11 Claims, 4 Drawing Sheets

(56) References Cited

U.S. PATENT DOCUMENTS

| | | | |
|---|---|---|---|
| 3,587,982 A * | 6/1971 | Campbell | 241/62 |
| 3,941,317 A * | 3/1976 | Kanor | 241/21 |
| 4,028,190 A * | 6/1977 | McAleer et al. | 435/289.1 |
| 4,072,275 A * | 2/1978 | Bartels et al. | 241/79 |
| 4,121,775 A * | 10/1978 | Roseberg et al. | 241/30 |
| 4,212,430 A * | 7/1980 | Dale et al. | 241/89.4 |
| 4,307,846 A * | 12/1981 | Spelsberg | 241/246 |
| 4,366,930 A * | 1/1983 | Trombetti, Jr. | 241/169 |
| 4,374,574 A * | 2/1983 | David | 241/169.1 |
| 4,505,433 A * | 3/1985 | Selenke | 241/46.01 |
| 4,514,091 A * | 4/1985 | Kaspar et al. | 366/130 |
| 4,569,612 A * | 2/1986 | Schwartzman et al. | 401/206 |
| 4,715,545 A * | 12/1987 | Hanifl et al. | 241/169.1 |
| 4,787,562 A * | 11/1988 | Templeton | 241/117 |
| 4,946,286 A * | 8/1990 | Purkapile | 366/247 |
| 5,067,666 A * | 11/1991 | Sussman | 241/36 |
| 5,261,613 A * | 11/1993 | Mullarky | 241/95 |
| 5,533,683 A * | 7/1996 | Fay et al. | 241/169 |
| 5,580,007 A * | 12/1996 | Caviezel et al. | 241/199.12 |
| 5,829,696 A * | 11/1998 | DeStefano et al. | 241/169 |
| 5,899,624 A * | 5/1999 | Thompson | 401/206 |
| 6,405,951 B1 * | 6/2002 | Wu | 241/169.1 |
| 6,509,187 B2 * | 1/2003 | Brem | 435/288.2 |
| 6,622,949 B1 * | 9/2003 | Baswick et al. | 241/36 |
| 7,165,734 B2 * | 1/2007 | Bucher | 241/199.12 |
| 7,225,920 B2 * | 6/2007 | Hoeffkes et al. | 206/222 |
| 7,490,976 B2 * | 2/2009 | Bucher | 366/247 |
| 7,520,458 B2 * | 4/2009 | Schulz | 241/101.4 |
| 7,699,252 B2 * | 4/2010 | Wu | 241/169.1 |
| 7,927,006 B2 * | 4/2011 | Bucher | 366/205 |
| 8,092,076 B2 * | 1/2012 | Bucher | 366/205 |
| 8,114,360 B2 * | 2/2012 | Bucher | 422/500 |
| 8,162,247 B2 * | 4/2012 | Faulker | 241/169.2 |
| 8,597,596 B2 * | 12/2013 | Daf | 422/534 |
| 2002/0118596 A1 * | 8/2002 | Mizutani et al. | 366/189 |
| 2004/0000605 A1 * | 1/2004 | McPherson et al. | 241/30 |
| 2004/0035964 A1 * | 2/2004 | Roggero | 241/169 |
| 2004/0196735 A1 * | 10/2004 | Barker et al. | 366/139 |
| 2004/0252582 A1 * | 12/2004 | Bucher | 366/273 |
| 2006/0013064 A1 * | 1/2006 | Bucher | 366/303 |
| 2006/0060686 A1 * | 3/2006 | Cheng | 241/169.1 |
| 2006/0076442 A1 * | 4/2006 | Fouse | 241/169.1 |
| 2007/0248499 A1 * | 10/2007 | Bucher | 422/101 |
| 2008/0253223 A1 * | 10/2008 | Bucher | 366/140 |
| 2009/0136384 A1 * | 5/2009 | Bucher | 422/100 |
| 2011/0171085 A1 * | 7/2011 | Bucher | 422/500 |

* cited by examiner

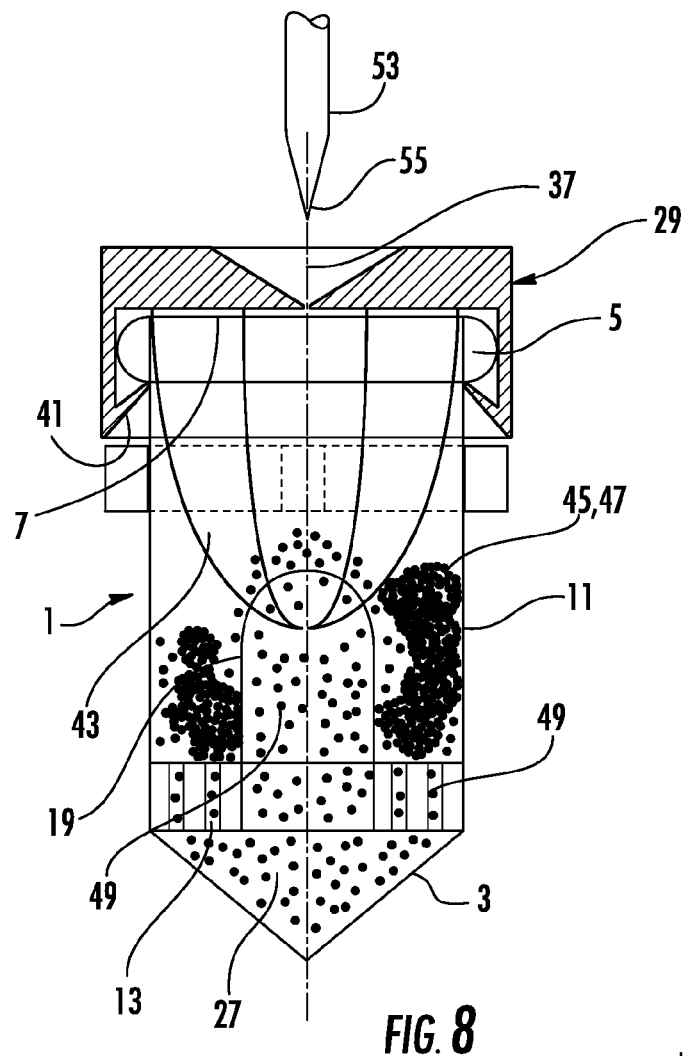
FIG. 8
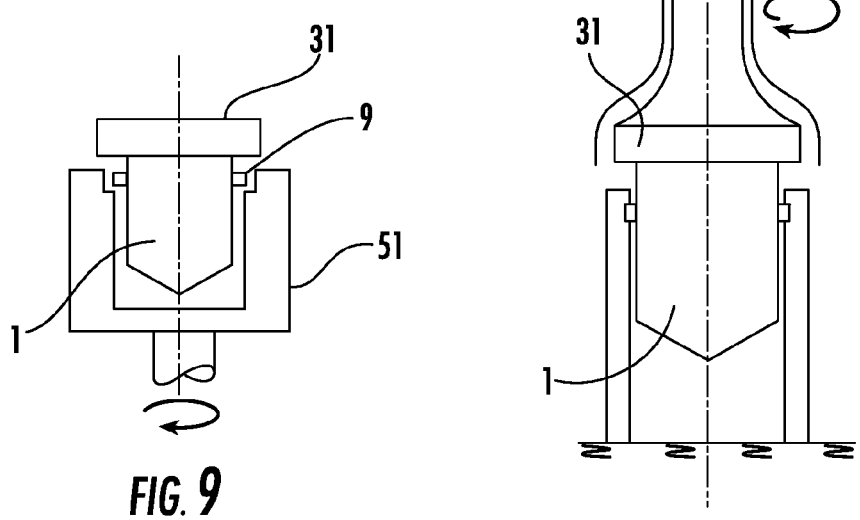
FIG. 9
FIG. 10

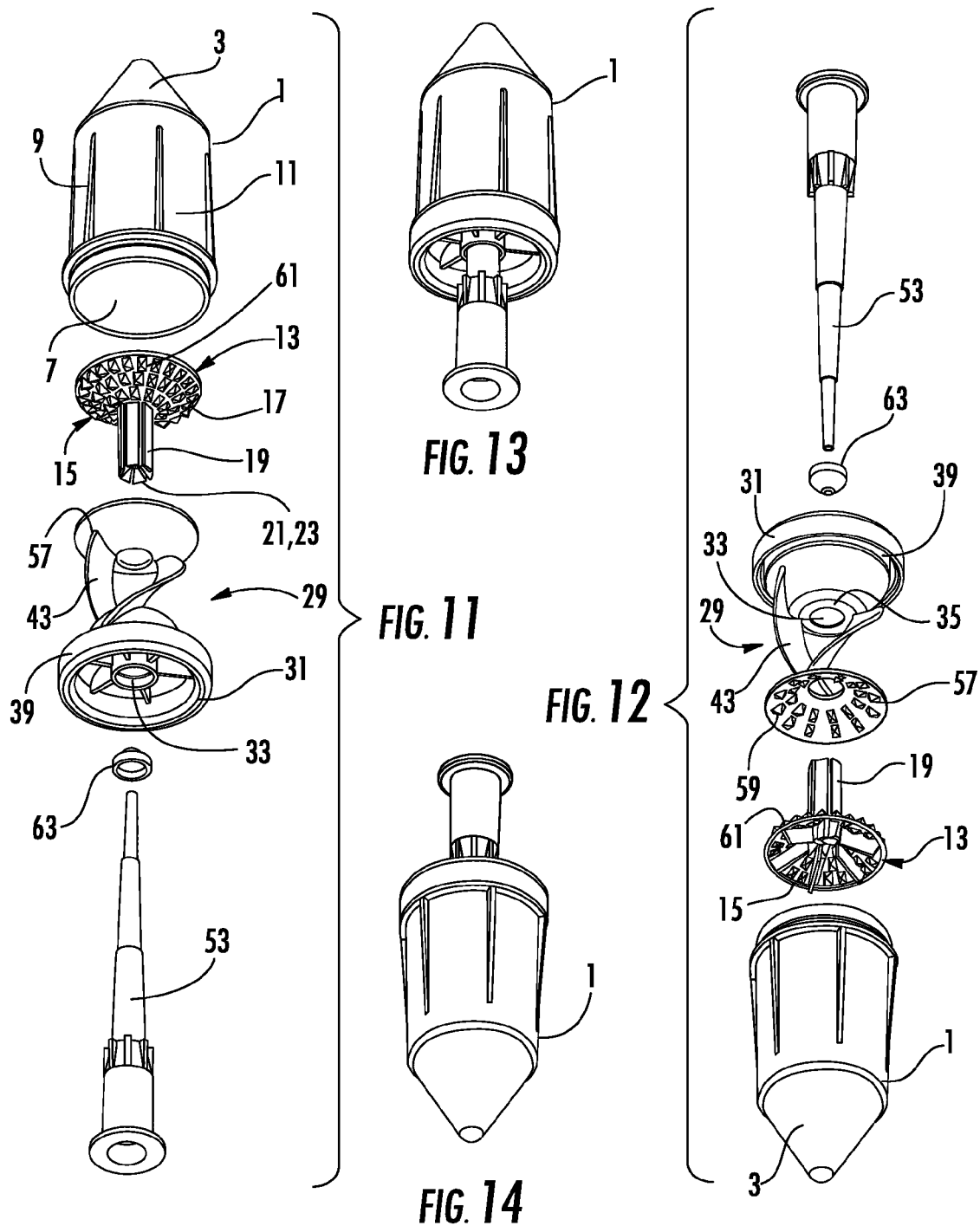

ONE-WAY MIXER HOMOGENIZER, EXTRACTOR, FRACTIONER OR SLURRY PRODUCER

BACKGROUND

The invention is directed to a single-use mixer, homogenizer, extractor, fractionater, or slurry producer of substances.

In laboratory operation various devices are known for mixing, homogenizing, extracting, fractionating or slurrying substances mostly to be processed in small amounts, in particular infectious, malodorous, chemically aggressive, or to be kept sterile ones.

Such a device is known from EP-B1 1361917 in which the laboratory test device and the agitating element form a unit and allow that, during processing of the substance, said substance cannot exit and contaminate the environment. The known device allows therefore to process the substance in a closed container and thus by the hermetical seal to avoid any infection, uncontrolled splashing, or spilling due to an accidental tipping of the laboratory test device.

SUMMARY

Based on this prior art the object of the present invention is to provide a single-use mixer, homogenizer, extractor, fractionater, or slurry producer in which a complete mixing and homogenization of substances and liquids that can be mixed is allowed, hermetically sealed while maintaining a certain grain size. Another object of the invention comprises that the insertion of liquids and the removal of the mixture or the homogenate can be performed after processing without opening the vessel.

This object is attained according to the invention by a single-use mixture, homogenizer, extractor, fractionater, or slurry producer according to the invention.

Advantageous embodiments of the device are described below.

By the design of the device according to the invention it is possible, after the insertion of the substance to be processed in the vessel, e.g., already on site where the substance is produced, to perform its processing entirely sealed and separated from the environment inside the device and subsequently to remove the product of the processing from the device without opening the device, i.e. without taking the lid off the laboratory test device. The device can be used for different tasks. Depending on the hole size and shape of the sieve serving as a cutter appropriately desired fractions can be achieved. The substance to be processed is separated from the environment during processing by a thin membrane and the membrane maintains this separation even when, after the removal of the substance, the removal tube of the pipette is pulled back out. Using an elastic compression element, the substance to be processed can be carefully pressed against the sieve and is successively guided through the bores in the sieve. Parts of the substance larger than the cross-section of the holes of the sieve are held back by the sieve so that below the sieve only the desired substance fractions to be processed can collect and be directly removed therefrom. The device is preferably made entirely from plastic and per se it can be disposed together with the still remaining, unnecessary or not useful substance portion. The rotary drive for the compression element or, in another embodiment of the invention, the vessel is not contaminated during processing of the substance and thus requires no cleaning.

The single-use mixer according to the invention can be directly filled in a slaughterhouse after tissue samples of animals have been taken from animals, for example and thus the tissue samples can be brought into the laboratory under sterile conditions. Necessary buffer solutions for further processing the tissue samples can subsequently be added in the laboratory through the lid plate and the membrane mounted thereto.

The single-use mixer also allows the content processed therein to be always hermetically sealed, leaving the fraction after fractioning in the mixer, allowing it to incubate (grow) and only later being removed for analysis. This also prevents that the tissue to be examined must be transferred from one vessel to another one between fractionating and the examination.

BRIEF DESCRIPTION OF THE DRAWINGS

Using an illustrated exemplary embodiment the invention is explained in greater detail. Shown are:

FIG. 8 an axial cross-sectional view through the vessel with a sieve and compression element inserted, FIG. 9 a view of a drive for the vessel, FIG. 10 a view of a drive for the compression element, FIG. 11 an exploded representation of the individual elements of the single-use mixer with the vessel above, FIG. 12 an exploded representation of the individual elements of the single-use mixer with the vessel below, FIG. 13 a view of a combined single-use mixer with a vessel above, and FIG. 14 a view of the combined single-use mixer with the vessel below.

DETAILED DESCRIPTION OF THE PREFERRED EMBODIMENTS

Figure 1:
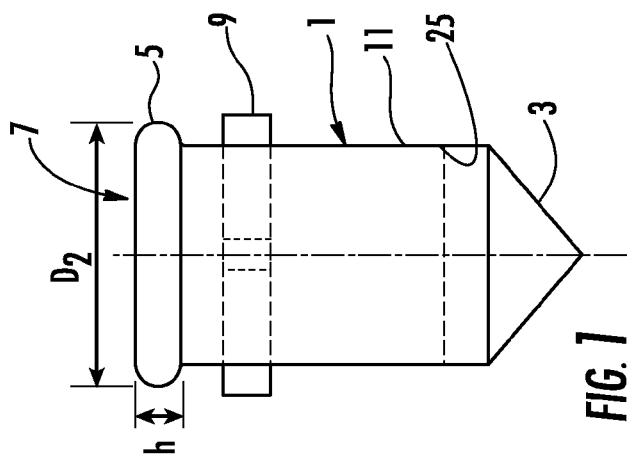
FIG. 1 an axial cross-sectional view through the vessel of the device.
Figure 2:
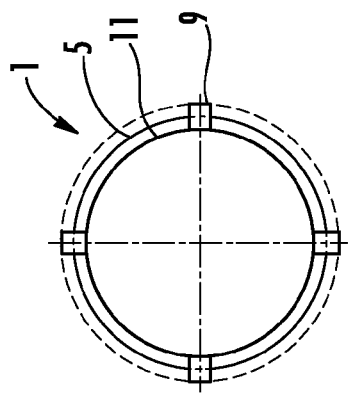
FIG. 2 a top view of the vessel in FIG. 1.
Figure 6:
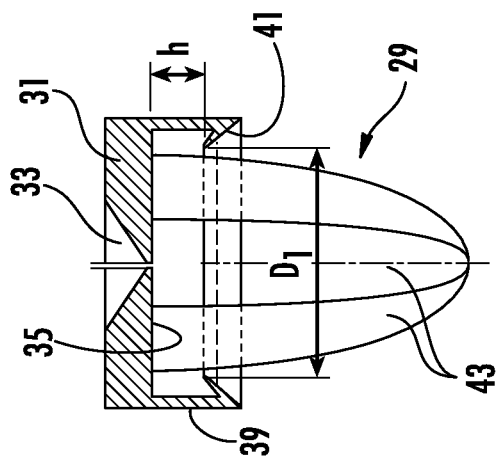
FIG. 6 an axial cross-sectional view through the compression element.
Figure 7:
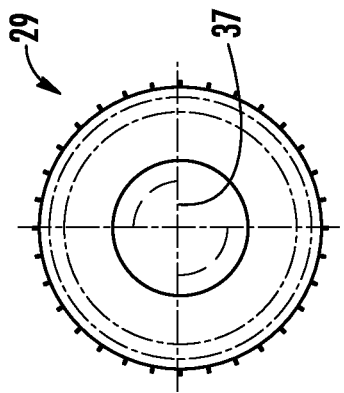
FIG. 7 a bottom view of the compression element.

In FIG. 1 a cylindrical laboratory test device, in the following called vessel 1 for short, is shown with a conically extending bottom 3 and a bead-shaped brim 5 in the area of the opening 7. At a distance from the brim 5, holding cams 9 are arranged distributed on the casing 11. Of course, more or less than four holding cams 9 may be provided. The cylindrical casing 11 and the bottom 3 of the vessel 1 are only shown in a single line for better visibility. The wall thickness depends on the size of the vessel and the quality of the plastic. The vessel 1 is preferably made from transparent plastic, so that the condition of the substance to the processed is visible. Instead of a conically extending bottom 3 on the vessel 1, a semi-spherical floor may be provided, too.

Figure 3:
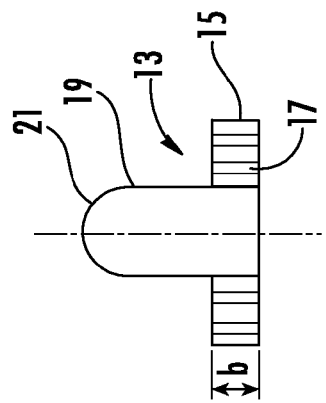
FIG. 3 a side view of the sieve.
Figure 4:
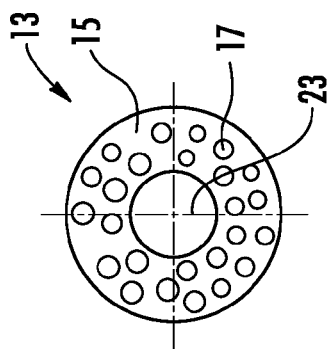
FIG. 4 a top view onto the sieve in FIG. 3.

FIGS. 3 and 4 show a sieve 13 serving as a part of a cutter and a ring-shaped plate 15 including essentially axially extending holes 17. All holes 17 may have the same diameter or holes 17 may be inserted with different diameters and irregular distribution over the ring-shaped surface (cf. particularly FIG. 4.)

In the center of the ring-shaped plate 15 with the holes 17, a cylinder 19 is arranged that protrudes upwardly, which is closed at the top with a hemi-spherical cap 21. The cap 21 may be embodied with a concave (FIG. 11) or convex (FIG. 3) shape and comprises a material that can be pierced by a pipette or, as shown in the figures, provided with cross-wise aligned slots 23 such that a pipette 53 can be pierced through the cap 21 without any great force. The slots 23 are preferably provided so fine that no substance to be processed, e.g., tissue, lymph or the like can penetrate from the top to the bottom in larger amounts.

Figure 5:
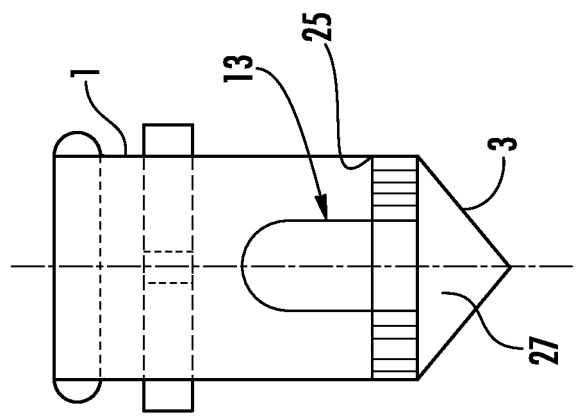
FIG. 5 an axial cross-sectional view through the vessel with an inserted sieve.

The plate 15, as shown in FIGS. 3 and 5, can be provided with a thickness s relatively great in reference to its diameter; however it may also be made generally thinner in contrast thereto (FIGS. 11 and 12). The sieve 13 with the cylindrical dome is preferably made from plastic. The sieve 13 may also be made from metal for fractioning cartilage material.

FIG. 5 shows the vessel 1 with the sieve 13 inserted above its bottom 3. The diameter of the sieve 13 is sized such that it can be inserted into the cylindrical vessel 1 and, when it has reached the bottom, is held in a friction-tight manner. Initially, in order to ensure the holding force of the sieve in the predetermined position, cam locks 25 can be arranged at the inside of the casing 11 of the vessel 1 distributed about the circumference. Instead of cam locks 25, encircling ribs may also be provided, which ensure the sieve 13 is held at an allocated position. In FIG. 5 it is further discernible that below the sieve 13, a pyramidal chamber develops, or for a hemi-spherical bottom 3, a correspondingly shaped hemi-spherical collection chamber 27.

FIGS. 6, 7, and 11, 12 show a compression element 29 simultaneously performing the function of a lid for the vessel 1. At a circular lid plate 31, in its center, for example a cone-shaped recess 33 is formed, with its tip almost reaching the bottom 35 of the lid plate 31. Radially extending slots 37 allow the lid plate 31 to be pierced with little force by a pipette. Alternatively to the slots 37, in the center of the lid plate 31, an area of the lid plate 31 may be made thin in the manner of a membrane.

A hollow-cylindrical casing section 39 is formed at the periphery of the lid plate 31, with a flange 41 protruding inwardly being arranged at its free edge. The diameter D1 of the flange 41, at its free, conically tapering edge, is smaller than the diameter D2 of the encircling brim 5 at the vessel 1. The distance of the free edge of the flange 41 from the bottom 35 of the lid plate 31 is approximately equivalent to the height h of the axial extension of the brim 5 at its root.

At the bottom 35 of the lid plate 31, additional elastic elements 43 are arranged, protruding away from the lid plate 31, which essentially extend beyond the casing section 39. The elastic elements 43 may also comprise striped flaps or helically extending rods. The function of the elastic elements 43 are explained in the following using FIG. 8, with the assembled device being shown in its entirety.

The opening 7 of the vessel 1 is closed by the lid plate 31 of the compression element 29. When the compression element 29 is placed onto the opening 7 of the vessel 1, the flange 41 glides beyond the brim 5. The edges of the flange 41 engage below the brim 5 and hold the compression element 29 connected to the vessel 1 in a sealing manner. The elastic elements 43 protrude into the interior of the vessel and press the materials to be processed, inserted into the vessel 1 prior to the placement of the compression element 29, to the surface of the sieve 13 past the cylinder 19 into the circular space between the casing of the cylinder 19 and the casing 11 of the vessel.

The black surfaces 47 in FIG. 8 represent unprocessed material 45, the black spots 49 are the already processed substances 45.

FIGS. 11 through 14 show views of the single-use mixer in accordance with another embodiment of the invention. In this embodiment, particularly the compression element 29 is provided with a milling plate 57 comprising a concave milling surface with milling teeth 59. The elements 43, named in the first exemplary embodiment with the reference character 43, are helically arranged and axially support the milling plate 57 at the lid plate 31 in an elastically spring-like manner. Here, the milling plate 57 is supported only by the elastic elements 43. The milling teeth 59 contact, when the single-use mixer is assembled, the teeth or protrusions 61 provided at the plate 15 of the sieve 13 in an elastic, springlike manner. The protrusions 61 and the holes 17 in the plate 15 may be arranged regularly or at irregular distances from each other. Further, in the second exemplary embodiment, in particular in FIG. 11, a sealing lid 63 is shown, which seals the recess 33 in the compression element 29. The sealing lid 63 is provided with a lid surface that is pierceable by the pipette 53.

In the following the operation of the device is explained in greater detail.

The operator fills the substances 45 to be processed into the vessel 1 through the opening 7. Substances 45 to be processed may be infectious, malodorous human or animal tissue. However, it may also comprise other solid matter, which for example has to be dissolved in smaller fractions or intensely mixed with other liquids, which are also added into the vessel 1.

After the insertion of the substance or substances 45 has been filled into the vessel 1, the compression element 29 is pushed onto the opening 7 and the flange 41 snaps below the brim 5. When the compression element 29 is placed on top the content is pressed by the elastic elements 43 via the cap 21 of the cylinder 19 into the circular space and contacts the surface of the sieve 13. In the second exemplary embodiment the content is pressed against the sieve 13 by the friction plate 57. Now the entire device is placed upon a suitable drive 51, which may be embodied cup-shaped and can snap to the cams 9. Either the lid plate 31 is held manually and the drive 51 is engaged, or from the top a holding element (not shown) is lowered to the lid plate 31 in order to hold it. Now, by the drive 51, the vessel 1 is rotated and the substance 47 is pressed by the fixed elastic elements 43 through the holes 17 into the collection chamber 27 or the vessel 1 is rotated and the compression element 29 is held. Therefore, only such fractions of the substance can enter the collection chamber that are either smaller than the diameter of the holes 17 or such that have been separated from the larger fractions by the sharp edges of the holes 17 or by the friction teeth 59. Now, when the small fractions 49 together with the usually added liquids enter the collection chamber 27, said chamber is successively filled and the mixture rises upwards in the cylinder 19 due to the pressure of the elastic elements 49 on the substances 45 located inside the vessel 1. Depending on the embodiment of the slots 37 in the cap 21 some of the fractions 49 or at least the liquid can exit again and is pressed through the sieve 13 for a second time. Chords and other unfragmented parts remain in the upper part of the vessel. Therefore in the lower part, the collection chamber 27, there are only the expected processed products. They may now be removed from the vessel via a pipette 53 without opening it. The tip 55 of the pipette 53 is first deployed through slots 37 into the lid plate 19 and then through the slots 23 into the cap 21 of the cylinder 19 to the collection chamber 27. Now the removal of the processed substances can occur without opening the vessel 1. The remaining unnecessary parts are disposed together with the device. Thus, they never again enter the environment after they have once been inserted into the vessel 1.

The invention claimed is:

1. A single-use mixer, homogenizer, extractor, fractionater, or slurry producer of substances comprising a vessel (1) with a closed bottom and a processing means (13) including two processing plates located in the vessel, that are axially pressed against one another in a spring-elastic manner via a spring (43), and the spring (43) is connected to and acts as a supporting member for an upper one of the processing plates so that the upper one of the processing plates is supported only by the spring (43) for rotatable movement relative to the other of the processing plates, the spring is also fixedly connected to a lid (31) of the vessel (1), and the lid (31) or the vessel (1) is adapted for connection to an external drive.

2. A single-use mixer according to claim 1, wherein the spring comprises two elastic elements (43) connected to the upper one of the processing plates which form a compression element (29) which contacts the other of the processing plates, which comprises a sieve (13), to press substances (45) located thereupon through said sieve (13).

3. A single-use mixer according to claim 2, wherein the elastic elements (43) comprise strip-shaped flaps or helically extending rods.

4. A single-use mixer according to claim 2, wherein the sieve (13) is provided with holes (17) having equal or different diameters.

5. A single-use mixer according to claim 2, wherein a lid (31) of the compression element (29) as well as the processing plates are provided with aligned penetrable areas (23, 27) that allow for insertion of a pipette from an external area into the closed bottom of the vessel.

6. A single-use mixer according to claim 1, wherein the spring comprises two elastic elements (43) connected to the upper one of the processing plates which comprises a milling plate (57), which contacts the other of the processing plates which comprises a sieve (13) to grind substances (45) trapped between the sieve (13) and the milling plate (57) and press them through the sieve (13).

7. A single-use mixer according to claim 6, wherein the elastic elements (43) comprise strip-shaped flaps or helically extending rods.

8. A single-use mixer according to claim 1, wherein the lid (31), the spring (43) and the upper one of the processing plates are formed as one piece.

9. A single-use mixer according to claim 1, wherein the upper processing plate comprises a milling plate (57) and the other of the processing plates comprises a sieve (13) having a plurality of protrusions thereon and holes defined therethrough.

10. A single-use mixer according to claim 9, wherein the sieve (13) further includes an axially centered upwardly protruding cylinder (19) which is closed at a top thereof with a cap (21) which is adapted for piercing with a pipette, the cylinder extending upwardly through an opening in the milling plate.

11. A single-use mixer according to claim 10, wherein the lid (31) comprises a central opening, and a sealing lid (63) which is adapted for piercing with a pipette is located therein, the cap (21) and the sealing lid (63) being located along a longitudinal axis of the vessel (1).

* * * * *